US00PP29439P3

(12) United States Plant Patent
Pressler

(10) Patent No.: US PP29,439 P3
(45) Date of Patent: Jul. 3, 2018

(54) LEMON TREE NAMED '7B97'

(50) Latin Name: *Citrus limon*
Varietal Denomination: 7B97

(71) Applicant: 2PH Farms Limited, Emerald, Queensland (AU)

(72) Inventor: Craig Robert Pressler, Emerald (AU)

(73) Assignee: 2PH Farms Limited, Emerald, Queensland (AU)

( * ) Notice: Subject to any disclaimer, the term of this patent is extended or adjusted under 35 U.S.C. 154(b) by 34 days.

(21) Appl. No.: 14/999,475

(22) Filed: May 10, 2016

(65) Prior Publication Data

US 2017/0332528 P1 Nov. 16, 2017

(51) Int. Cl.
*A01H 5/08* (2018.01)

(52) U.S. Cl.
USPC ..... Plt./201
CPC ..... *A01H 5/0806* (2013.01)

(58) Field of Classification Search
USPC ..... Plt./201
See application file for complete search history.

(56) References Cited

PUBLICATIONS

Plant Varieties Journal, Quarter One, vol. 20, No. 1, pp. 44,95,96,230-233, May 16, 2007.*

* cited by examiner

*Primary Examiner* — Keith O Robinson
(74) *Attorney, Agent, or Firm* — Michelle Bos Legal LLC

(57) ABSTRACT

'7B97' is a new and distinct lemon tree notable for its high quality seedless fruit.

3 Drawing Sheets

Genus and species: *Citrus limon.*
Variety denomination: '7B97'.

BACKGROUND AND SUMMARY OF THE VARIETY

The new lemon variety '7B97' originated as an induced mutation of 'Eureka' lemon (not patented). Gamma irradiation from a Gammacell 200 (60C) source was applied to bud sticks of 'Eureka' in 1998 at Emerald, Queensland, Australia. The irradiated bud sticks were budded onto 'Carrizo' rootstock (not patented) in 1998 at Bundaberg, Queensland, Australia, and the trees that survived were field planted at Bundaberg in 1999. The selection now known as '7B97' was identified as showing consistently fewer seeds than the parent variety, with no significant reduction in fruit size. A comparative trial was planted in 2003, using '7B97' budwood on 'Benton' (not patented) rootstock. Successive generations have consistently shown few seeds and have reproduced true to type.

'7B97' is a new and distinct lemon tree notable for its fruit, which produces consistently low numbers of seeds. Table 1 shows a comparison of '7B97' lemon to 'Eureka' and other similar (unpatented) varieties.

TABLE 1

Comparison of '7B97' to Known Varieties

| Characteristic | '7B97' | '3 ELS 0' | 'Eureka' |
|---|---|---|---|
| Seed quantity | Absent to few | Absent to few | Many |
| Mean fruit length (mm) | 81.92 | 74.56 | 84.76 |
| Mean fruit diameter (mm) | 60.64 | 57.16 | 62.84 |

TABLE 1-continued

Comparison of '7B97' to Known Varieties

| Characteristic | '7B97' | '3 ELS 0' | 'Eureka' |
|---|---|---|---|
| Fruit length/diameter ratio | 1.35 | 1.31 | 1.35 |
| Rind thickness (mm) | 4.92 | 4.48 | 5.24 |

BRIEF DESCRIPTION OF THE PHOTOGRAPHS

Figure 1:
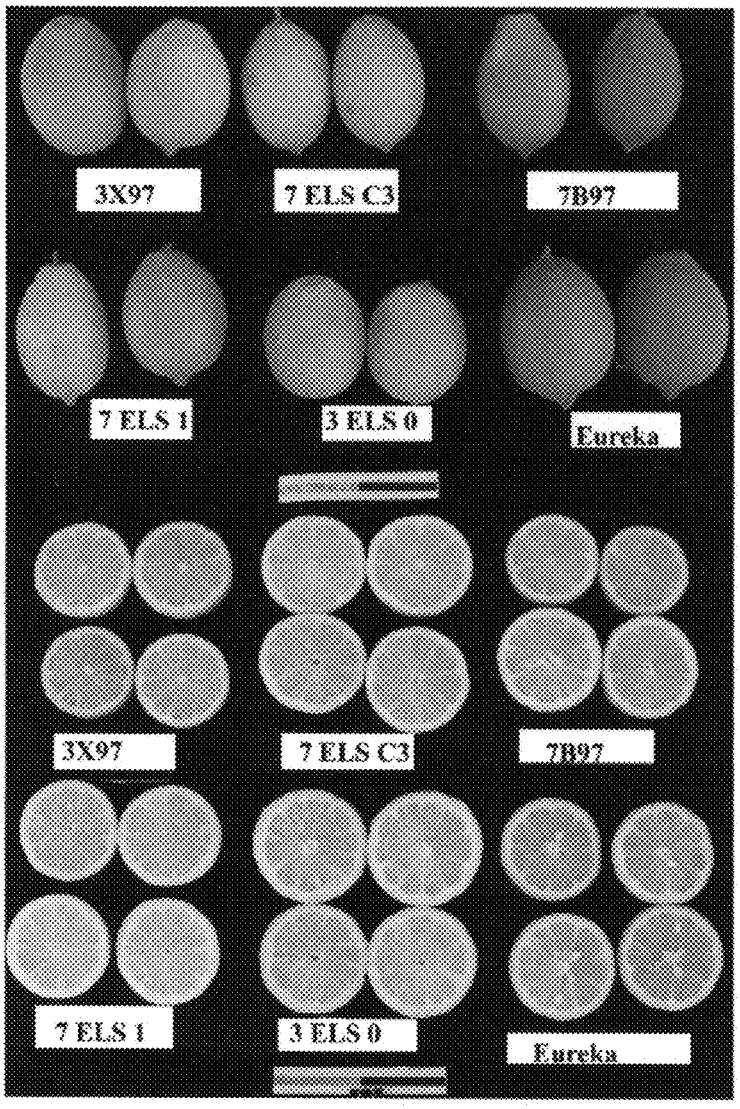
FIG. 1 shows whole and sectioned fruit of '7B97' lemon and other varieties.
Figure 2:
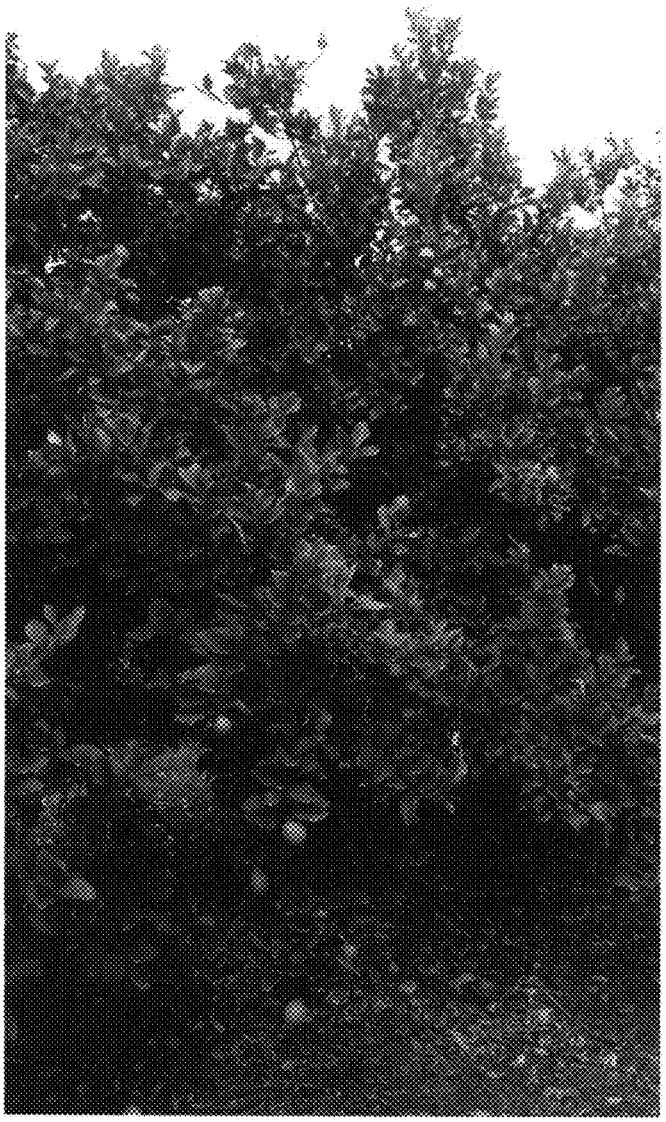
FIG. 2 shows a '7B97' lemon tree.
Figure 3:
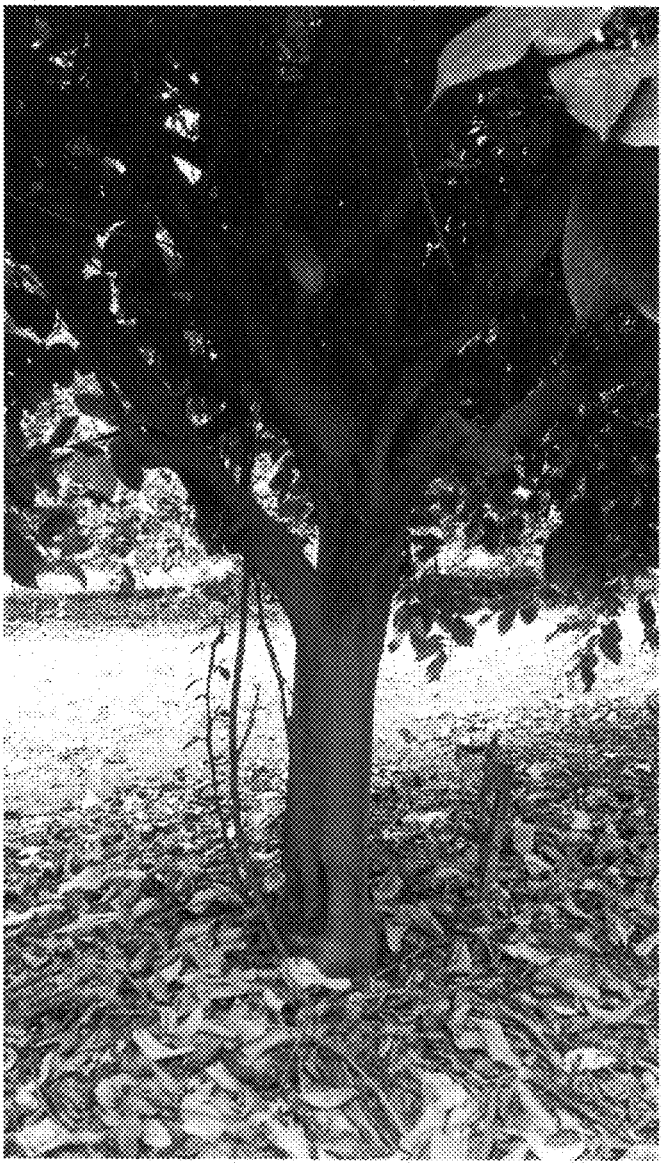
FIG. 3 shows the trunk, branches and leaves of a '7B97' lemon tree.

The tree shown in FIGS. 2 and 3 is an eleven year old tree planted in 2003. Because lighting conditions can affect the colors shown in photographic illustrations, color characteristics of this new variety should be determined with reference to the observations described herein, rather than from the illustrations alone.

DETAILED BOTANICAL DESCRIPTION

The following detailed botanical description is based on observations of trees and fruit of '7B97', budded to 'Benton' rootstock (not patented) and planted in 2003. Observations were recorded and photographs taken during the 2006 and 2014 growing seasons at Mundubbera, Queensland, Australia. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average. Colors are described with reference to The Royal Horticultural Society Colour Chart (5th edition, 2007).

Tree:

*Vigor*.—Vigorous.
*Density of canopy*.—Very dense, open center.
*Habit*.—Upright spreading.
*Height*.—4 m.
*Spread*.—3 m.
*Trunk diameter* (*at* 30 *cm above graft*).—148 mm.
*Bark texture*.—Smooth.
*Bark color*.—Greyed-orange 163D, greyed-purple N187A.
*Lenticel size*.—1 mm.
*Lenticel color*.—Greyed-purple N187A.
*Lenticel quantity*.—Many, 2 to 4 per $cm^2$.
*Tendency toward alternate bearing*.—None.
*Winter hardiness*.—Same as 'Eureka', performs well in USDA hardiness zone 9 and 10.
*Chilling requirement*.—Same as 'Eureka', no chilling requirement.
*Drought tolerance*.—Same as 'Eureka', tolerant.

Branch (fruiting branch located about 1 m above graft union):

*Length*.—80 cm.
*Diameter*.—6.1 cm.
*Crotch angle*.—Approximately 30 degrees.
*Bark color*.—Greyed-orange 163D, greyed-purple N187A.
*Bark texture*.—Smooth.
*Thorns*.—Present, few.
*Thorn length*.—Less than 5 mm.

Current year shoot:

*Length*.—80 cm.
*Color*.—Green 140A.

Blossoms:

*Bud shape*.—Oval.
*Bud length*.—2.1 mm.
*Bud diameter*.—1 mm.
*Bud color*.—Yellow-green 144A.
*Quantity of blossoms per cluster*.—4 to 7.
*Blossom diameter*.—22 mm.
*Blossom depth*.—20 mm.
*Pollen*.—None.
*Sepal length*.—4.3 mm.
*Sepal width*.—4.4 mm.
*Sepal shape*.—Arched.
*Sepal margin*.—Smooth.
*Sepal color*.—Upper surface — Yellow 2B.
*Sepal color*.—Lower surface — Yellow 3B.
*Quantity of petals per flower*.—5.
*Petal shape*.—Elongated arch.
*Petal apex*.—Rounded to acute.
*Petal margin*.—Smooth.
*Petal length*.—14 mm.
*Petal width*.—4.9 mm.
*Petal color*.—Upper surface — White NN155D.
*Petal color*.—Lower surface — White NN155D, violet 84D.
*Date of first bloom*.—Late August.
*Date of full bloom*.—Early September.
*Flowering habit*.—More than once in a season; up to 7 flowerings observed.
*Date of first fruitlet fall*.—November.
*Pedicel length*.—4.6 mm.
*Pedicel diameter*.—2.0 mm.
*Pedicel color*.—Yellow-green 151C.
*Pistil quantity per flower*.—1.
*Pistil length*.—12.0 mm.
*Pistil color*.—Orange 26A, yellow 9A, yellow-green 144A.
*Anther quantity per flower*.—1.
*Anther length*.—2.5 mm.
*Anther color*.—Orange 26A.
*Stigma quantity per flower*.—1.
*Stigma length*.—2.1 mm.
*Stigma color*.—Yellow 9A Green.
*Style quantity per flower*.—1.
*Style length*.—8.1 mm.
*Style color*.—Yellow 1B.
*Ovary quantity per flower*.—1.
*Ovary length*.—5.5 mm.
*Ovary diameter*.—2.6 mm.
*Ovary color*.—Yellow-green 144A.

Leaves:

*Length*.—98.1 mm.
*Width*.—49.6 mm.
*Length/width ratio*.—1.97.
*Blade margin*.—Crenate.
*Leaf shape*.—Oval, weak concave.
*Apex shape*.—Acute.
*Base shape*.—Cuneate.
*Color of upper surface*.—Green 143B.
*Color of lower surface*.—Yellow-green 145A.
*Anthocyanin coloration in young leaf*.—Weak, less intense than 'Eureka'.
*Leaf texture* (*upper surface*).—Smooth.
*Petiole length*.—12.5 mm.
*Petiole diameter*.—2.7 mm.
*Petiole color*.—Yellow-green N144D.
*Wings*.—None.

Fruit:

*Quantity per cluster*.—3.
*Axial diameter*.—81.92 mm.
*Apical diameter*.—60.64 mm.
*Weight*.—153 g.
*General shape in profile*.—Oval.
*Position of maximum diameter*.—Middle of fruit.
*Navel*.—None.
*Neck*.—Present, very short.
*Nipple*.—Present, weakly prominent.
*Rind color*.—Green 140B.
*Glossiness*.—Weak.
*Oil glands per $cm^2$*.—About 40.
*Oil gland diameter*.—1 mm.
*Oiliness*.—Oily.
*Rind thickness*.—4.92 mm.
*Ease of peeling*.—Difficult.
*Rind texture*.—Smooth.
*Albedo thickness*.—5 mm.
*Albedo color*.—Yellow 2C.
*Quantity of fruit segments per fruit*.—8.8 (average of 25 fruit).
*Toughness of segment membrane*.—Moderate.
*Juice sac length*.—8 mm.
*Juice sac shape*.—Cylinder.

*Juice sac length to width ratio*.—8:1.4.
*Juice sac color*.—Yellow 2C.
*Flesh color*.—Yellow 2C.
*Juice soluble solids* (° *brix*).—7.7.
*Relative harvest maturity* (*early, late, etc.*).—Early.
*Harvest window* (*date range*).—January through December.
*Seeds present*.—None or very few.
*Stem length*.—20 mm.
*Stem diameter*.—3 mm.
*Stem color*.—Yellow-green 144B.
*Parthenocarpy*.—Absence.

Diseases and pests: No distinguishing resistance or susceptibility noted.
Harvest yield: 50 to 100 Tons per hectare.
Market use: Fresh.
Keeping quality: Same as 'Eureka'.
Shipping quality: Same as 'Eureka'.

The invention claimed is:

1. A new and distinct variety of lemon tree, substantially as illustrated and described herein.

* * * * *